(12) United States Patent
Sedazzari

(10) Patent No.: US 11,474,340 B2
(45) Date of Patent: Oct. 18, 2022

(54) BORESCOPE PROBE

(71) Applicant: OPTO ENGINEERING S.P.A., Mantova (IT)

(72) Inventor: Claudio Sedazzari, Mantova (IT)

(73) Assignee: OPTO ENGINEERING S.P.A., Mantova (IT)

(*) Notice: Subject to any disclaimer, the term of this patent is extended or adjusted under 35 U.S.C. 154(b) by 0 days.

(21) Appl. No.: 16/943,685

(22) Filed: Jul. 30, 2020

(65) Prior Publication Data
US 2022/0043252 A1 Feb. 10, 2022

(30) Foreign Application Priority Data

Jul. 14, 2020 (IT) .................. 202020000004198

(51) Int. Cl.
*G02B 23/24* (2006.01)
*A61B 1/00* (2006.01)

(52) U.S. Cl.
CPC ...... *G02B 23/2446* (2013.01); *A61B 1/00163* (2013.01); *A61B 1/00174* (2013.01); *G02B 23/2423* (2013.01); *G02B 23/2461* (2013.01); *G02B 23/2484* (2013.01)

(58) Field of Classification Search
USPC ............................................ 356/241.1–241.5
See application file for complete search history.

(56) References Cited

U.S. PATENT DOCUMENTS

| 4,976,524 A | 12/1990 | Chiba |
| 7,465,271 B2 * | 12/2008 | Kanazawa ......... A61B 1/00096 600/160 |
| 2011/0001984 A1 | 1/2011 | Keller et al. |
| 2012/0296165 A1 * | 11/2012 | Segawa ................. A61B 1/041 600/109 |
| 2015/0087912 A1 * | 3/2015 | Vogel ................. A61B 1/00195 600/162 |
| 2016/0077315 A1 | 3/2016 | Trubko et al. |
| 2019/0227298 A1 * | 7/2019 | Elmaanaoui ....... A61B 1/00177 |

* cited by examiner

*Primary Examiner* — Darryl J Collins
(74) *Attorney, Agent, or Firm* — Thomas | Horstemeyer, LLP

(57) ABSTRACT

A borescope probe for inspecting a side wall of a cavity includes a primary mirror, a main refractive optical group, a stop, and a sensor plane. The primary mirror collects light rays diffused by a surface of the side wall of the cavity according to an inlet angle (α) and reflects the light rays towards the refractive optical group. The main refractive optical group is placed between the primary mirror and the sensor plane and is suitable to receive the light rays reflected by the primary mirror and focus them on the sensor plane.

18 Claims, 2 Drawing Sheets

BORESCOPE PROBE

CROSS REFERENCE TO RELATED APPLICATION

This application claims priority to and benefit of Italian Patent Application No. 202020000004198 filed Jul. 14, 2020, the contents of which are incorporated by reference in their entirety.

FIELD OF THE INVENTION

The present invention relates to a borescope probe, i.e. a probe designed to inspect the side walls of cavities having increased lengths in relation to the diameter, or which are difficult to reach with regular optical and light systems. The optics can be directly inserted into the object to be inspected by using the borescope probe.

SUMMARY OF THE INVENTION

An object of the present invention is to provide a visual inspection device capable of inspecting the side wall of a cavity having an increased length with respect to the diameter thereof.

Another object of the present invention is to provide a borescope probe having a sturdy structure which is easy to maintain.

Yet another object of the present invention is to provide a borescope probe capable of focusing the image very accurately.

Such objects are achieved by a borescope probe as described and claimed herein.

BRIEF DESCRIPTION OF THE FIGURES

The technical features of the invention according to the aforesaid objects can be clearly found in the contents of the claims hereinbelow and the advantages thereof will become more apparent from the following detailed description, made with reference to the accompanying drawings which show one or more embodiments merely given by way of non-limiting example, in which:

DETAILED DESCRIPTION

Figure 1:
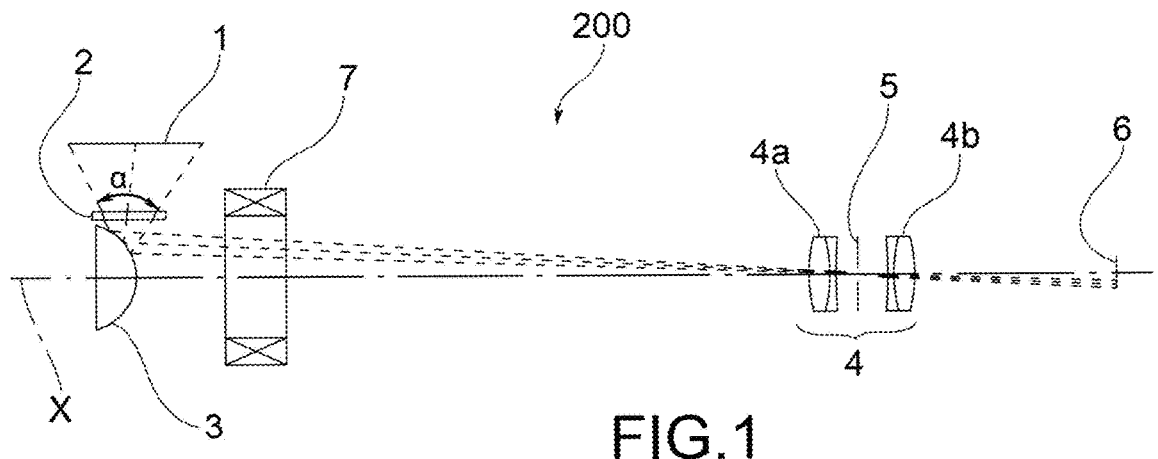
FIG. 1 is an optical diagram of a first embodiment of a borescope probe according to the present invention.

Possible exemplary embodiments of a borescope probe according to the present invention are indicated, as a whole, in the drawings by 200; 200'; 200".

In the following description, elements which are common to the different embodiments of the probe are indicated by the same reference numerals.

In a general embodiment, the borescope probe 200; 200'; 200" comprises a probe body 100 which extends along an optical probe axis X. The probe body 100 supports a primary mirror 3, a main refractive optical group 4, a stop 5, and a sensor plane 6.

The primary mirror 3 is positioned at a distal end of the probe body so as to be introduced into a cavity of which the side wall 1 is to be inspected. The primary mirror 3 is suitable to collect the light rays diffused by a surface of the side wall 1 of the cavity which is substantially parallel to the optical probe axis X according to an inlet angle α and reflect the light rays towards the main refractive optical group 4.

Figure 4:
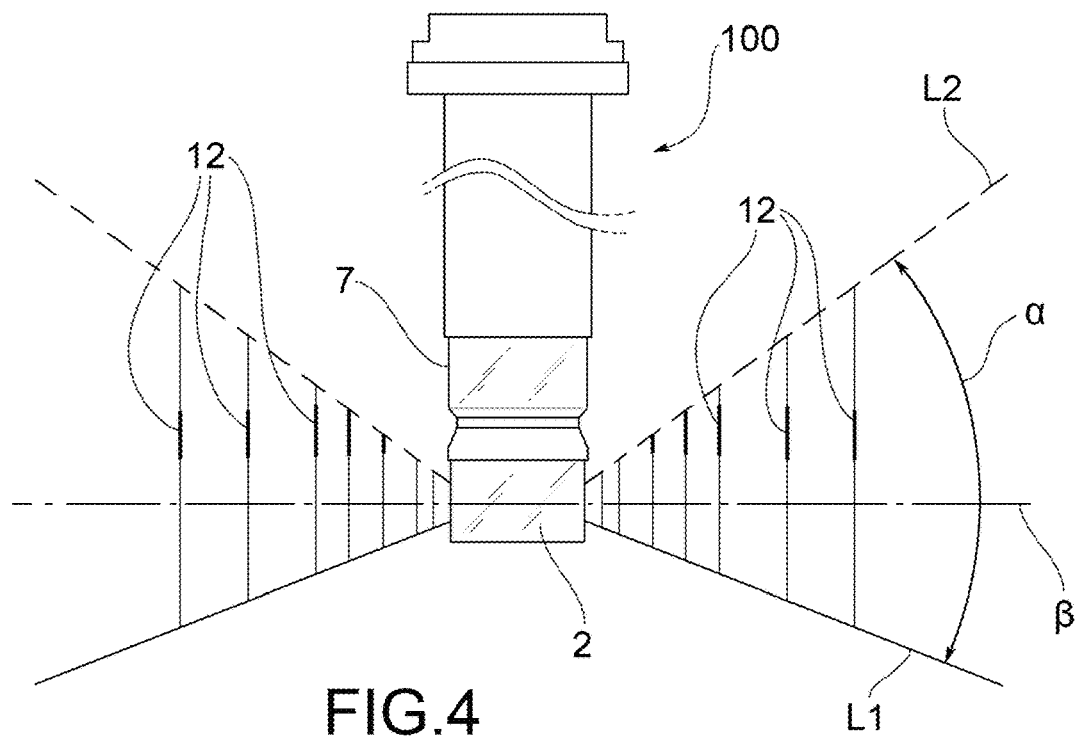
FIG. 4 is a diagrammatic depiction of the operation of the borescope probe according to the present invention.

In other words, a zero plane β orthogonal to the optical probe axis X taken as a reference, the primary mirror 3 is configured to collect light rays which form positive angles and negative angles with respect to the zero plane, as illustrated in detail in FIG. 4.

The main refractive optical group 4 is placed between the primary mirror 3 and the sensor plane 6 and is suitable to receive the rays reflected by the primary mirror 3 and focus them on the sensor plane 6.

In an embodiment, the primary mirror 3 is convex in shape, e.g. spherical, with convexity facing the main refractive optical group 4.

In an embodiment, the main refractive optical group 4 comprises at least two lenses 4a, 4b.

In an embodiment, stop 5 is positioned between the lenses 4a 4b of the main refractive optical group 4.

The term "stop" indicates, in a conventional manner, the hole serving the function of limiting the intensity of the light transmitted to the sensor plane 6.

In a variant, stop 5 is positioned in front of or behind the main refractive optical group 4.

In an embodiment, the borescope probe comprises a safety window 2 made of clear material, including glass, to protect at least the primary mirror 3. The safety window 2 may protect the inner components of the probe from dust.

In an embodiment, the probe body 100 further supports a light source 7, including an LED source, suitable to light the wall of the cavity to be inspected. There are no restrictions on the range of wavelengths which can be used. The position and the type of lighting depend on the use. Lighting may be direct or scattered.

In an embodiment, the inlet angle (α) has a width between 40° and 80°. A typical range for the inlet angle is about 70°, but it may be varied according to various design needs. The inlet angle may be selected by modifying the shape of the primary mirror 3 and/or the main refractive optical group 4.

With regards to the sensor plane 6, the width thereof depends on the chamber used to collect the images. Sensors having various sizes can be accommodated by changing the focus distance of the main refractive optical group 4.

Figure 2:
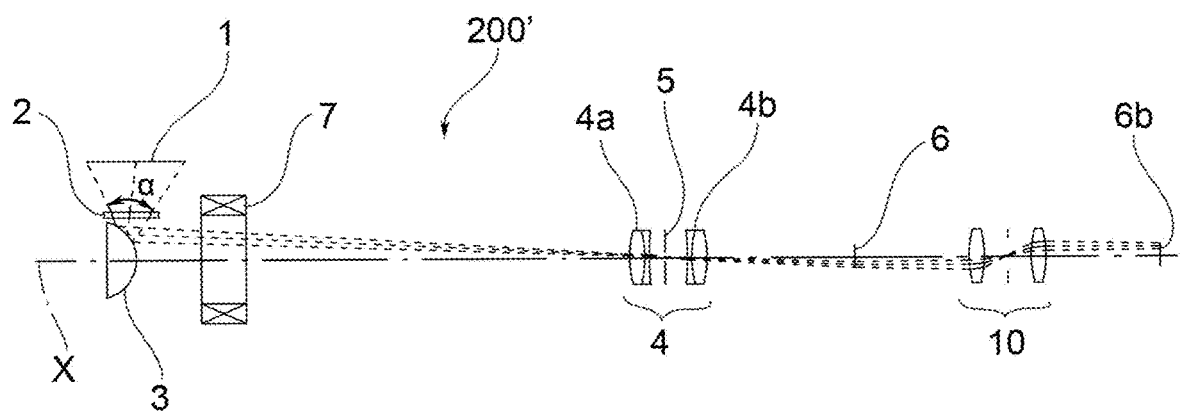
FIG. 2 is an optical diagram of a second embodiment of a borescope probe according to the present invention.

In an embodiment shown in FIG. 2, the borescope probe 200' comprises a secondary refractive optical group 10, also called optical relay group, placed between the main refractive optical group 4 and the sensor plane 6b. Such a secondary optical group 10 is configured to collect the image formed by the main refractive optical group 4 and focus it on the sensor plane 6b. The secondary optical group 10 may be used when the length of the measuring head of the probe is to be lengthened. Indeed, it is worth noting in FIG. 2 that the image collected by the secondary optical group 10 from the primary optical group 4 is brought on a sensor plane 6b translated backwards (and possibly transversely as well) with respect to the sensor plane 6 associated with the main optical group 4 alone.

In an embodiment, the secondary refractive optical group 10 has a unitary enlargement and therefore does not modify the size of the image. However, relay groups with enlargement other than 1 can also be designed.

Possible methods of focusing the probe are now described. The focusing procedure is performed to obtain the best results according to the cavity to be inspected. The term "focusing" indicates the procedure that allows the maximum possible definition of the image projected onto the sensor plane 6; 6*b* to be obtained. The best focus point closely depends on the diameter of the cavity and on the inlet angles of the light rays. According to the optical and/or mechanical configuration, the following focusing procedures can be implemented in the probe.

Manual focusing. Here, focusing is performed by modifying the distance of the sensor plane 6 with respect to the whole system. Therefore, the borescope probe is provided with means for adjusting the position of the sensor plane 6. Spacers may be provided, which are inserted into or removed from the group mechanics of the sensor plane 6.

Mechanical focusing. Here, the distance between the sensor plane and the whole optical system is carried out by means of a mechanism capable of varying the position of the main refractive optical group 4 with respect to the primary mirror 3 and the sensor plane 6. In this embodiment, the probe is therefore provided with means for adjusting the position of the main refractive optical group 4.

Figure 3:
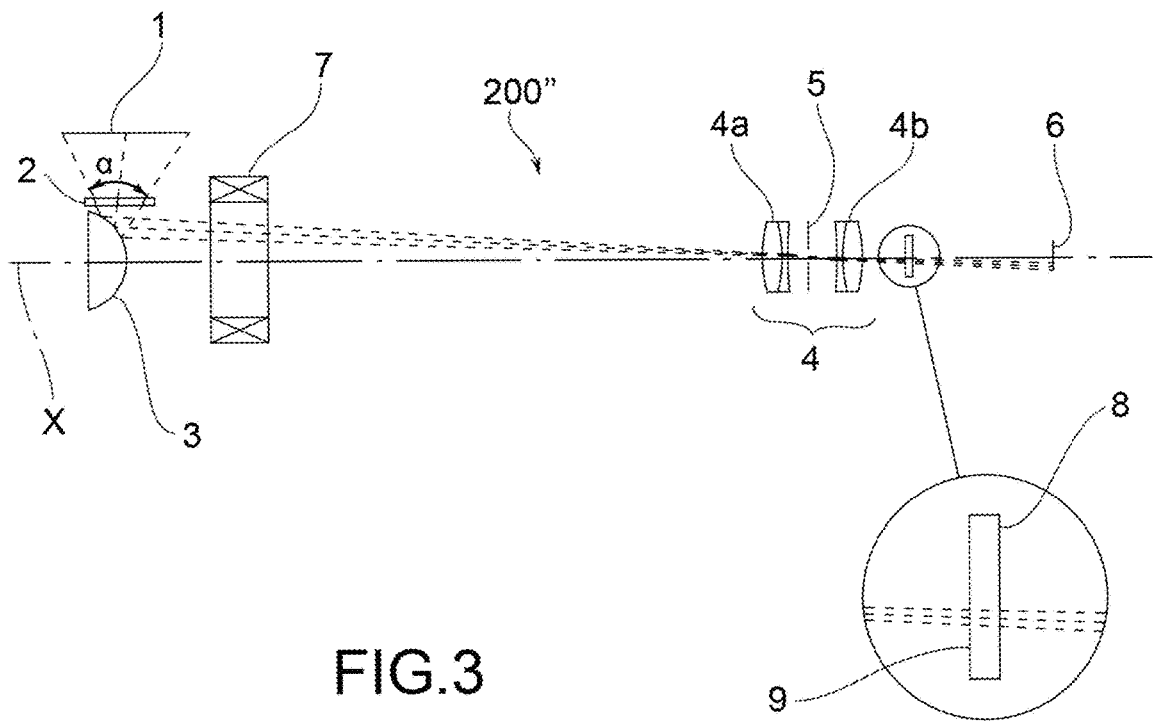
FIG. 3 is an optical diagram of a third embodiment of a borescope probe according to the present invention.

Focusing by means of adaptive lens. In an embodiment shown in FIG. 3, the borescope probe 200″ comprises an adaptive lens 8, 9 placed between the main refractive optical group 4 and the sensor plane 6 or in front of the main refractive optical group 4. The adaptive lens 8, 9 is electrically controllable to adjust the focus of the probe. In particular, a lens 8 is inserted, which is capable of modifying the shape of one of the surfaces 9 thereof by applying an electric current. This mechanism can be controlled via software to perform focusing by means of artificial vision algorithms. The best position of the adaptive element may depend on the features of the main refractive optical group 4. According to the design and the desired specifications, the adaptive lens can be inserted in front of the main refractive optical group 4, between the lenses 4*a* and 4*b* of the main refractive optical group 4, and behind the main refractive optical group 4.

The probe is configured to be easily repaired in case of damage. In an embodiment, the primary mirror 3 and the safety window 2 can form a single body which can easily be replaced in case of impact.

The probe body 100 can further be provided with a connection interface to robotic arms.

FIG. 4 is a diagrammatic depiction of the operation of the borescope probe 200; 200'; 200″. In the example shown, the probe has a diameter of 21 mm and can inspect cavities with inner diameters ranging from 25 mm to 100 mm. In this example, a side wall having maximum extension equal to 53 mm can be inspected with a height of 9 mm of the primary mirror 3 and with an inlet angle α of 60°.

FIG. 4 further indicates 12 particular zones of the image in which there can be direct reflection between the light source 7 and the observation point. The presence of this reflection allows increased transfer of light power to be obtained, and therefore particular types of surface inspection to be performed in order to search for three-dimensional irregularities on the surface observed (e.g. scratches, inclusions, bubbles).

Figure 5:
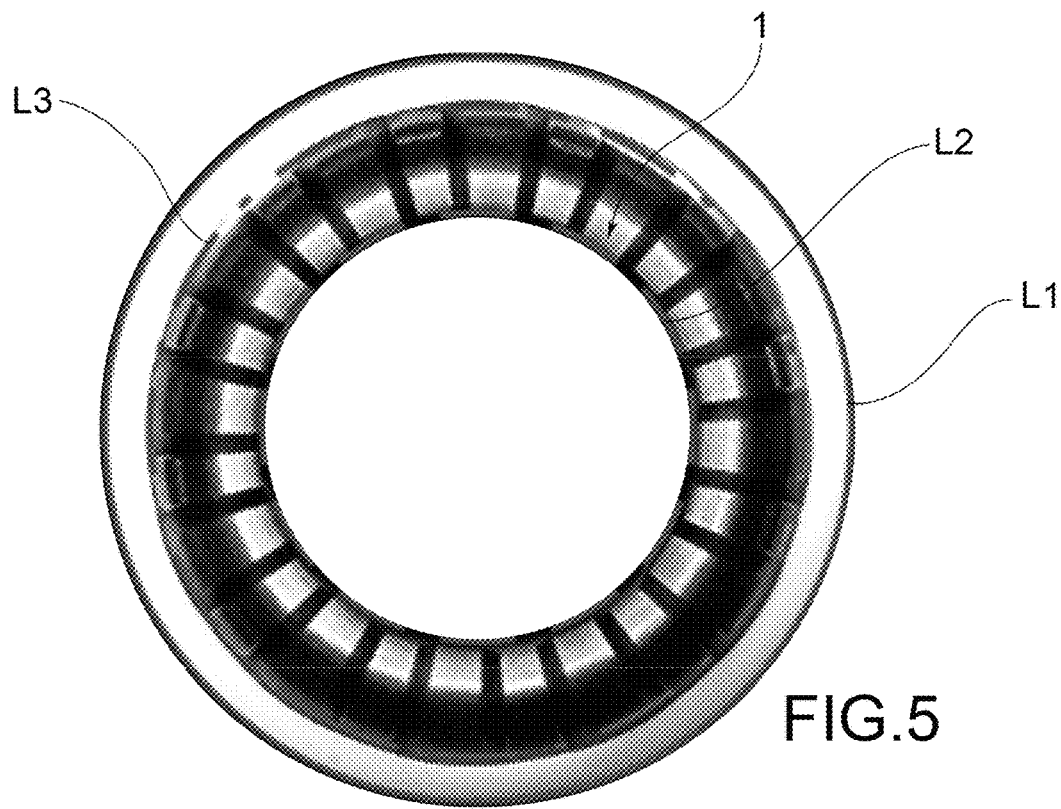
FIG. 5 is the image generated by the probe as it is projected onto the sensor plane.

FIG. 5 is an image example of the side wall 1 of a cavity as it is received by the sensor plane 6; 6*b*. With reference also to FIG. 4, the continuous outer line L1 indicates the bottom of the cavity (−22.5°, the dotted line L2 shows the upper view (+37.5°, the dash-dotted line L3 relates to the side view, i.e. to the zero plane β.

As can be noted in FIG. 5, the side area 1 of the cavity to be inspected is projected as a circular crown onto the sensor plane 6; 6*b*. Due to digital processing algorithms, the "unwrapping" procedure can be performed, and the real proportions of the object can be restored in order to correctly analyze it (FIG. 5*a*).

Figure 5A:
FIG. 5a is the image generated by the probe after digital processing.

Therefore, in an embodiment, the borescope probe comprises digital hardware and software processing means operatively connected to the sensor plane (6; 6*b*) and configured to transform the circular crown image acquired by the sensor plane into a linear extension image (FIG. 5*a*).

Therefore, the present invention achieves the preset goals.

Obviously, the practical embodiment thereof can also take other shapes and configurations than that shown above without departing from the scope of protection as described and claimed herein.

Moreover, all the details may be replaced by technically equivalent elements, and any sizes, shapes and materials may be used according to various needs.

What is claimed is:

1. A borescope probe for inspecting a side wall of a cavity, the borescope probe comprising a probe body extending along an optical probe axis, a primary mirror, a main refractive optical group, a stop, and a sensor plane which are supported by the probe body, wherein:
   the primary mirror is positioned at a distal end of the probe body to be introduced into the cavity, the primary mirror being suitable to collect light rays diffused by a surface of the side wall of the cavity which is substantially parallel to the optical probe axis according to an inlet angle, and reflect said light rays towards the main refractive optical group;
   the main refractive optical group is placed between the primary mirror and the sensor plane and is suitable to receive the light rays reflected by the primary mirror and focus them on the sensor plane; and
   further comprising an adaptive lens placed between the main refractive optical group and the sensor plane or in front of the main refractive optical group, and electrically controllable to adjust focus of the borescope probe.

2. The borescope probe of claim 1, wherein the primary mirror is convex in shape, with convexity facing the main refractive optical group.

3. The borescope probe of claim 2, wherein the primary mirror is spherical in shape with convexity facing the main refractive optical group.

4. The borescope probe of claim 1, wherein the main refractive optical group comprises at least two lenses.

5. The borescope probe of claim 4, wherein the stop is positioned between the at least two lenses of the main refractive optical group.

6. The borescope probe of claim 1, wherein the stop is positioned in front of or behind the main refractive optical group.

7. The borescope probe of claim 1, further comprising a safety window made of clear material, including glass, to protect at least the primary mirror.

8. The borescope probe of claim 1, further comprising a light source supported by the probe body and suitable to light the side wall of the cavity to be inspected.

9. The borescope probe of claim 1, wherein the inlet angle has a width between 40° and 80°.

10. The borescope probe of claim 1, further comprising a secondary refractive optical group placed between the main refractive optical group and the sensor plane and configured to collect a circular crown image formed by the main refractive optical group and focus it on the sensor plane.

11. The borescope probe of claim 1, further comprising digital hardware and software processing means operatively connected to the sensor plane and configured to transform a circular crown image acquired by the sensor plane into a linear extension image.

12. A borescope probe for inspecting a side wall of a cavity, the borescope probe comprising a probe body extending along an optical probe axis, a primary mirror, a main refractive optical group, a stop, and a sensor plane which are supported by the probe body, wherein:
- the primary mirror is positioned at a distal end of the probe body to be introduced into the cavity, the primary mirror being suitable to collect light rays diffused by a surface of the side wall of the cavity which is substantially parallel to the optical probe axis according to an inlet angle, and reflect said light rays towards the main refractive optical group;
- the main refractive optical group is placed between the primary mirror and the sensor plane and is suitable to receive the light rays reflected by the primary mirror and focus them on the sensor plane; the main refractive optical group consists of two doublets and the stop is positioned between the two doublets of the main refractive optical group; and further comprising a secondary refractive optical group placed between the main refractive optical group and the sensor plane and configured to collect a circular crown image formed by the main refractive optical group and focus it on the sensor plane.

13. The borescope probe of claim 12, wherein the primary mirror is convex in shape with convexity facing the main refractive optical group.

14. The borescope probe of claim 12, wherein the stop is positioned in front of or behind the main refractive optical group.

15. The borescope probe of claim 12, further comprising a safety window made of clear material, including glass, to protect at least the primary mirror.

16. The borescope probe of claim 12, further comprising a light source supported by the probe body and suitable to light the side wall of the cavity to be inspected.

17. The borescope probe of claim 12, wherein the inlet angle has a width between 40° and 80°.

18. The borescope probe of claim 12, further comprising digital hardware and software processing means operatively connected to the sensor plane and configured to transform the circular crown image acquired by the sensor plane into a linear extension image.

* * * * *